United States Patent [19]
Kruger, Jr. et al.

[11] Patent Number: 5,220,105
[45] Date of Patent: Jun. 15, 1993

[54] PROCESS FOR PURIFYING D-LIMONENE

[75] Inventors: Albert J. Kruger, Jr.; Mark L. Corkum; Steven G. Carlson, all of Altamonte Springs; Don H. Kimball, Winter Haven, all of Fla.

[73] Assignee: The Coca-Cola Company, Atlanta, Ga.

[21] Appl. No.: 857,518

[22] Filed: Mar. 25, 1992

[51] Int. Cl.$^5$ .................... C07C 7/00; C07C 7/10
[52] U.S. Cl. ..................... 585/855; 585/856; 585/858; 585/868
[58] Field of Search ............... 585/858, 868, 856, 855

[56] References Cited

U.S. PATENT DOCUMENTS

| | | | |
|---|---|---|---|
| 3,778,485 | 12/1973 | Prochazka | 585/868 |
| 3,862,014 | 1/1975 | Atkins et al. | 202/161 |
| 4,140,690 | 2/1979 | Dolhyj et al. | 502/300 |
| 4,497,838 | 2/1985 | Bonnell | 426/429 |
| 4,533,487 | 8/1985 | Jones | 252/170 |
| 4,818,250 | 4/1989 | Whitworth | 44/62 |
| 4,915,707 | 4/1990 | Whitworth | 44/62 |

*Primary Examiner*—Anthony McFarlane
*Attorney, Agent, or Firm*—Willian Brinks Olds Hofer Gilson & Lione

[57] ABSTRACT

A process is provided for the purification of d-Limonene, particularly to remove odorous impurities. The process includes the step of mixing d-Limonene with an oxidizer and separating the oxidizer from the d-Limonene. In preferred embodiments, the d-Limonene is then mixed with an acid and separated. The preferred process also includes a wash water step. The oxidizer and acid are preferably provided in aqueous solutions. The process removes the odorous impurities without the formation of an off-color in the d-Limonene.

20 Claims, 1 Drawing Sheet

5,220,105

PROCESS FOR PURIFYING D-LIMONENE

BACKGROUND OF THE INVENTION

The present invention relates to a process for purifying d-Limonene, and in particular to a process for treating d-Limonene to remove odorous impurities therein.

d-Limonene is a naturally occurring, cyclic, olefinic, oil material found in citrus peels, having the basic formula $C_{10}H_{16}$. d-Limonene is produced as a byproduct of processes used to make citrus products, such as frozen concentrated orange juice.

In a typical citrus processing plant, the citrus peels are squeezed to remove as much moisture as possible before being sent to a dryer where the peels are dried to produce an animal feed. The liquid squeezed from the peels is known as press liquor. Most typically, the press liquor is treated by a distillation process. The vapor phase from this process includes water and the d-Limonene, which are condensed and separated. The remainder is referred to as molasses. Sometimes d-Limonene is referred to as stripper oil because it is produced by stripping the press liquor.

d-Limonene has a number of uses. Traditionally, d-Limonene was mixed with fuel oils and used as a boiler fuel. In this regard, see U.S. Pat. Nos. 4,818,250 and 4,915,707 to Whitworth which disclose processes for purifying d-Limonene to avoid the formation of gums so that it can be blended with conventional petroleum fuels for motor, diesel and aviation fuel.

Another use for d-Limonene is to make glue. d-Limonene is also used in the production of aromatic compounds. U.S. Pat. No. 4,533,487 to Jones discloses a process for blending d-Limonene to produce a multi-use cleansing agent. Recently, d-Limonene has found utility as a replacement for fluorocarbons in cleaning solid state electronic parts.

Many of these uses of d-Limonene require a high purity product, and such high-purity products command a premium price. d-Limonene produced at citrus processing plants, however, quite commonly has odorous impurities which prevent it from being sold at the premium price. It is believed that these impurities result because of high temperatures used in the distillation operation, and possibly because the molasses has begun to burn on to the insides of the tubes through which the press liquor is fed during the distillation operation. One solution to the problem might therefore be to lower the distillation temperature. This, however, reduces the throughput capacity of the equipment, and additional equipment involves a large capital expenditure.

During the development of the present invention another problem was encountered. Sometimes d-Limonene treated to remove these odorous impurities ended up with off-color problems, which also prevented it from being sold at the highest possible price. Hence, there is a need for a process for treating d-Limonene to remove odorous impurities that preferably will not result in off-color d-Limonene.

SUMMARY OF THE INVENTION

Applicants have discovered a process for purifying d-Limonene by treating the d-Limonene with an oxidizer and then separating the oxidizer from the d-Limonene. The oxidizer reacts with the odorous impurities. It has been found that the use of an oxidizer removes the impurities without leading to the formation of off-color problems.

In preferred embodiments, the invention comprises the steps of mixing d-Limonene with an aqueous oxidizer solution, separating the aqueous oxidizer from the d-Limonene, mixing the resulting d-Limonene with an aqueous acid solution and separating the aqueous acid solution from the d-Limonene. An additional wash water step may be used to remove any remaining acid.

The invention and its advantages will best be understood in light of the following description and example, and in view of the drawing, a brief description of which is as follows.

DETAILED DESCRIPTION OF THE DRAWING AND PREFERRED EMBODIMENTS OF THE INVENTION

Figure 1:
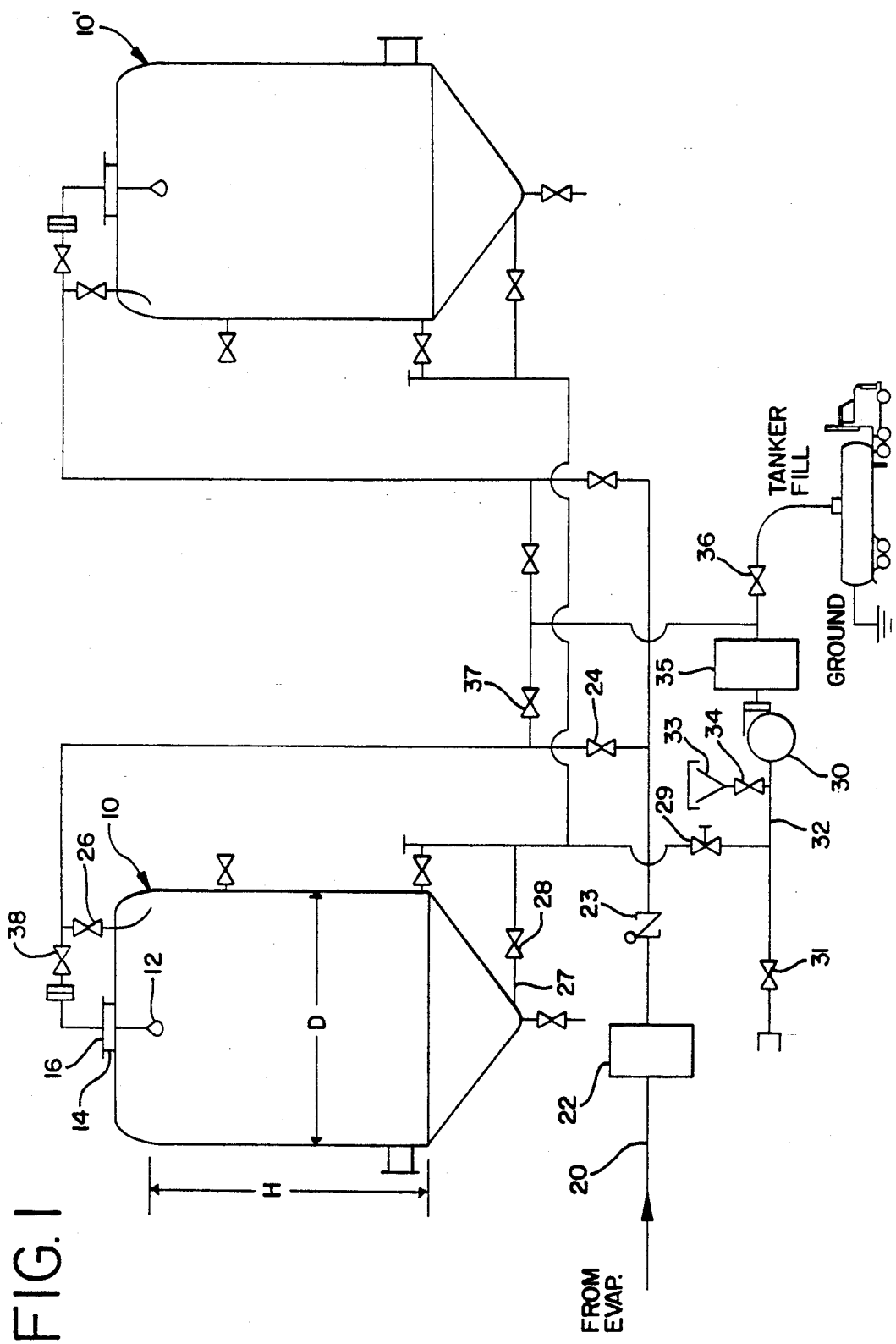
FIG. 1 depicts an equipment setup that may be used to practice the process of the present invention.

Unless specified otherwise, all percentages herein are weight percents.

The present invention involves purifying d-Limonene by mixing it with an oxidizer and separating the oxidizer from the d-Limonene. In preferred embodiments of the invention, the oxidizer is provided in an aqueous solution. This form for the oxidizer helps in both the mixing and separating steps.

The oxidizer is preferably one that will form a caustic medium in water. The preferred oxidizers are sodium hypochlorite, calcium hypochlorite, lithium hypochlorite, magnesium hypochlorite and potassium hypochlorite. Some oxidizers are not believed to be strong enough, such as potassium permanganate, and would take an excessive time to react. Other oxidizers, such as hydrogen peroxide, could cause polymerization of the d-Limonene. The preferred oxidizer used should not increase the peroxide content of the d-Limonene to a peroxide value above 1. The most preferred oxidizer, in terms cost and effectiveness, is sodium hypochlorite, with calcium hypochlorite also being a good choice.

The preferred concentration of the oxidizer solution is between about 0.14 and about 1.4 molar. For sodium hypochlorite, this would be a concentration range of about 1% to about 10%, with a 5.25% solution (which is commonly available as a bleach) being most preferred.

The oxidizer is mixed with the d-Limonene at a ratio of about 27 moles to about 270 moles of oxidizer per 1000 gallons of d-Limonene. Using a 5.25% sodium hypochlorite solution, this amounts to mixing the oxidizer solution at a volume ratio of 1 part oxidizer solution to between about 10 and about 100 parts of d-Limonene.

The oxidizer is mixed with the d-Limonene so that it can react with the odorous impurities. When the oxidizer is provided in an aqueous solution form, the mixing can easily take place by agitating the mixture so as to have good contact with the d-Limonene. Since d-Limonene is an oil and has a specific gravity (about 0.84) less than that of water, the aqueous solution will settle to the bottom of the d-Limonene.

Thus the mixing requires agitation to mix the two layers or phases.

When provided in an aqueous solution form, the oxidizer can easily be separated from the d-Limonene by letting the mixture stand. It has been found that after good mixing, a small layer of an emulsion will form between the aqueous and d-Limonene layers. If desired, this emulsion may be broken to recover the d-Limonene in the emulsion.

In preferred embodiments of the invention, an aqueous acid solution is next mixed with the d-Limonene. The acid is used to neutralize any caustic left in the d-Limonene from the step of mixing the oxidizer and d-Limonene. Again, the acid is preferably added in a solution form to facilitate mixing and separation of the acid and d-Limonene.

The acid may be any acid suitable for mixing and separation from d-Limonene. Preferred acids include hydrochloric acid, sulfuric acid and phosphoric acid. Hydrochloric acid was found to perform the best but can attack stainless steel equipment that may be used for the process. Sulfuric acid must be handled carefully because of its hazard potential. Phosphoric acid is preferred, primarily from its cost and availability standpoint. The addition of an acid solution has been found to break any emulsion left over from the oxidation solution mixing step of the process.

The acid will be mixed at a level of about 6.5 moles to about 65 moles per 1000 gallons of d-Limonene. Preferred acid solutions will have a concentration of about 1% to about 5% acid in the water. Preferably, the acid solution will be mixed at a volume ratio of 1 part acid solution to between about 10 and about 100 parts of d-Limonene. The mixing and separation procedures can be the same as those used with the oxidizer solution.

Preferably after being mixed with an acid solution, the d-Limonene will be treated with a final wash water mixing step. This step helps remove any acid that may remain in the d-Limonene. The washing step may also be effective in some instances to remove caustic residue, and might be used in lieu of the acid mixing step since in many places tap water is slightly acidic.

In the wash water step, preferably tap water is added to the d-Limonene at a volume ratio of 1 part water to between about 1 and about 50 parts d-Limonene. Again, mixing and separation can be carried out by agitating the mixture and letting it stand to separate into a two-phase system.

The time required for the mixing steps is dependent on the strength of the solution used, the severity of agitation and the volume of solution and d-Limonene being treated. The time required for the mixture to stand is dependent on the degree of mixing. Generally, the oxidizer solution and wash water separate fairly quickly from the d-Limonene. The time periods in the following example are good approximations.

EXAMPLE 1

Example 1 used the equipment system setup shown in FIG. 1.

The setup in FIG. 1 shows two tanks 10 and 10' set up with a variety of interconnecting piping and valves. The example only used one of the tanks 10 to carry out all of the mixing steps. Reference will be made only to those parts of the setup which were actually used. The tank 10 had a diameter D of 9 feet 6 inches and a height H of 16 feet. Inside of the tank was a spray ball 12. The tank 10 was a closed tank with a manhole access 14, fitted with a cover 16. The tank had a 8500 gallon capacity.

d-Limonene from the distillation equipment (evaporators) was introduced to the tank 10 via line 20, filter 22, a check valve 23 and valves 24 and 26. Filter 22 was used to remove any large particles in the d-Limonene. The tank 10 included a valve 28 at the exit 27 through which the tank 10 was drained. Fluid from valve 28 passed through valve 29 where it could either be pumped by pump 30 or discharged via valve 31. The line 32 leading to pump 30 was fitted with a funnel 33 and valve 34 so that materials could be added to the system. Another filter 35 was used after the pump 30 to remove any particles introduced through funnel 33. After filter 35, fluid could either be directed through valve 36 into a tanker or through valve 37 back to the top of tank 10. When the material was to be introduced into tank 10 through spray ball 12, valve 26 was closed and valve 38 was opened.

8000 gallons of d-Limonene were collected in tank 10. The d-Limonene had a "smoky note" aroma contamination.

168 gallons of an aqueous solution of 5.25% sodium hypochlorite was poured into funnel 33 and pumped into tank 10 via valves 37 and 26. This solution, being more dense than the d-Limonene, settled to the bottom of the tank. Valve 26 was then closed and valve 38 was opened. Valves 28 and 29 were opened and pump 30 was activated so that the contents from the bottom of the tank were circulated and sprayed out of spray ball 12 at the top of the tank. At first only the sodium hypochlorite solution was circulated, but as the solution mixed with the d-Limonene, eventually both materials were pumped through the spray ball 12. Pump 30 was allowed to run for about 1 hour. The mixture was then allowed to stand unagitated for about 30 minutes. The sodium hypochlorite solution collected in an aqueous phase on the bottom of tank 10, with the d-Limonene on top. A small layer of an emulsion formed in between the two layers. The valves 28, 29 and 31 were opened to drain the tank until this emulsion layer started to exit from the tank, at which time the valves were closed.

An acid solution was prepared by diluting an 85% concentrated phosphoric acid solution with water to produce a phosphoric acid content of 1.77% by weight. 200 gallons of the diluted acid were added to tank 10 via funnel 33, valve 34, pump 30 and valves 37 and 26. The acid settled to the bottom of tank 10. The appropriate valves were opened, pump 30 was activated and the contents of the tank were circulated and sprayed out of spray ball 12 for approximately 6 hours. The emulsion formed during the oxidizer solution mixing operation broke upon contact with the acid. The acid solution—d-Limonene mixture was next allowed to stand for about 2 hours. The acid solution was drained from the tank 10 via valves 28, 29 and 31. To determine when the acid solution was all drained and d-Limonene was starting to drain from the tank, the contents being drained were measured, and when almost 200 gallons had been drained, the contents were drained into a bucket. When d-Limonene started to drain, it formed an oil slick on top of the acid solution in the bucket.

The d-Limonene in tank 10 was then treated with 400 gallons of wash water. The water was added to tank 10 and pump 30 was activated, circulating the contents of the tank for about 4 hours. At the end of this time period pump 30 was shut off and the mixture was allowed to stand for about a half hour. The water was then drained from tank 10 via valves 28, 29 and 31, again until an oil slick was noticed in a bucket into which the last of the water was drained.

The resulting d-Limonene was free of the "smoky note" odor it originally had, was clear and free of off-color, and could be sold at a premium price.

The above example, with a few modifications, represents the preferred embodiment of the invention. Rather than using a spray ball and a circulating pump to mix the various solutions, it would be preferably to use a mechanical agitator in the tank 10 to get good contact between the aqueous and oil phases. A suitable agitator is the Model N33 fixed mounting propeller type Lightning ® mixer from Mixing Equipment Co., Inc. With better agitation, the mixing times could be reduced considerably. However, for large size batches it is expected that the minimum mixing time for each step would be about 20 minutes. Another way of achieving the desired agitation would be to pass air bubbles up through the tank 10.

The invention has been found to provide consistent purification of d-Limonene without the formation of off-color. In earlier work using sodium hydroxide instead of an oxidizer, it was found that if the sodium hydroxide solution was used at a concentrated level to provide quick results, the d-Limonene often ended up having an off-color problem, making it unsalable at the premium price.

It should be appreciated that the methods of the present invention are capable of being incorporated in the form of a variety of embodiments, only a few of which have been illustrated and described above. The invention may be embodied in other forms without departing from its spirit or essential characteristics. The described embodiments are to be considered in all respects only as illustrative and not restrictive, and the scope of the invention is, therefore, indicated by the appended claims rather than by the foregoing description. All changes which come within the meaning and range of equivalency of the claims are to be embraced within their scope.

We claim:

1. A process for purifying d-Limonene containing odorous impurities comprising the steps of:
   a) mixing an oxidizer with the d-Limonene and
   b) separating the oxidizer from the d-Limonene to thereby produce a deodorized d-Limonene that has a peroxide value not greater than 1.

2. The process of claim 1 wherein the oxidizer is selected from the group consisting of sodium hypochlorite, calcium hypochlorite, lithium hypochlorite, magnesium hypochlorite, potassium hypochlorite and mixtures thereof.

3. The process of claim 1 wherein the oxidizer comprises sodium hypochlorite.

4. A process for purifying d-Limonene to remove odorous impurities comprising the steps of:
   a) mixing the D-Limonene and an aqueous solution of an oxidizer;
   b) separating the aqueous oxidizer solution from the d-Limonene;
   c) mixing the d-Limonene from step b) with an aqueous solution of an acid; and
   d) separating the aqueous acid solution from the d-Limonene,
   e) steps a)–d) being effective to deodorize the d-Limonene.

5. The process of claim 4 further comprising the steps of mixing wash water with the d-Limonene resulting from step d) and separating the wash water from the d-Limonene.

6. The process of claim 4 wherein the oxidizer is selected from the group consisting of sodium hypochlorite, calcium hypochlorite, lithium hypochlorite, magnesium hypochlorite, potassium hypochlorite and mixtures thereof.

7. The process of claim 4 wherein the oxidizer comprises sodium hypochlorite.

8. The process of claim 4 wherein the acid is selected from the group consisting of phosphoric acid, sulfuric acid, hydrochloric acid and mixtures thereof.

9. The process of claim 4 wherein the acid solution comprises phosphoric acid.

10. The process of claim 4 wherein the oxidizer solution is mixed with the d-Limonene at a volume ratio of oxidizer solution:d-Limonene of between about 1:100 and about 1:10.

11. The process of claim 4 wherein the acid solution is mixed with the d-Limonene at a volume ratio of acid solution:d-Limonene of between about 1:100 and about 1:10.

12. The process of claim 4 wherein the oxidizer solution has an oxidizer concentration of between about 1% and about 10%.

13. The process of claim 4 wherein the acid solution has an acid concentration of between about 1% and about 5%.

14. The process of claim 5 wherein the wash water is mixed with the d-Limonene at a volume ratio of wash water:d-Limonene of between about 1:50 and about 1:1.

15. The process of claim 4 wherein the oxidizer solution concentration and the ratio of oxidizer solution to d-Limonene is such that the ratio of oxidizer to d-Limonene is between about 27 moles and about 270 moles per 1000 gallons of d-Limonene.

16. The process of claim 4 wherein the acid solution concentration and the ratio of acid solution to d-Limonene is such that the ratio of acid to d-Limonene is between about 6.5 moles and about 65 moles per 1000 gallons of d-Limonene.

17. A process for removing odorous impurities from d-Limonene without causing color changes comprising the steps of:
   a) mixing an oxidizer solution of about 1% to about 10% sodium hypochlorite or calcium hypochlorite in water with d-Limonene at a ratio of between about 10 and about 100 gallons of oxidizer solution per 1000 gallons of d-Limonene;
   b) agitating the oxidizer—d-Limonene mixture for at least 20 minutes;
   c) allowing the oxidizer—d-Limonene mixture to stand to form an aqueous oxidizer phase and a d-Limonene layer;
   d) separating the aqueous oxidizer phase from the d-Limonene;
   e) mixing an acid solution of about 1% to about 5% phosphoric acid, sulfuric acid or hydrochloric acid in water with the d-Limonene separated during step d) at a ratio of between about 10 and about 100 gallons of acid solution per 1000 gallons of d-Limonene;
   f) agitating the acid—d-Limonene mixture for at least 20 minutes;
   g) allowing the acid—d-Limonene mixture to stand to form an aqueous acid phase and a d-Limonene layer;
   h) separating the aqueous acid phase from the d-Limonene;

i) mixing wash water with the d-Limonene separated in step h) at a ratio of about 20 to about 1000 gallons of wash water per 1000 gallons of d-Limonene;

j) agitating the was water—d-Limonene mixture for at least 20 minutes;

k) allowing the wash water—d-Limonene mixture to stand to form an aqueous wash water phase and a d-Limonene layer; and m) steps a)–l) being effective to deodorize the d-Limonene.

18. The method of claim 17 wherein the agitation in at least one of steps b), f) and J) is provided by a mechanical agitation in a tank.

19. The method of claim 17 wherein the agitation in at least one of steps b), f) and J) is provided by passing air bubbles through the mixture.

20. The method of claim 17 wherein the agitation in at least one of steps b), f) and j) is provided by circulating the mixture through a pump connected to the bottom of the tank and spraying the mixture into the top of the tank.

* * * * *

UNITED STATES PATENT AND TRADEMARK OFFICE
CERTIFICATE OF CORRECTION

PATENT NO. : 5,220,105
DATED : June 15, 1993
INVENTOR(S) : Kruger, Jr. et al.                Page 1 of 2

It is certified that error appears in the above-identified patent and that said Letters Patent is hereby corrected as shown below:

In column 2, line 41, after "terms" insert --of both--.

In column 2, please merge line 63 with line 64 and make a continuous paragraph.

In column 3, line 21-22, replace "solution mixing" with --solution-mixing---.

In column 3, line 62, insert --10-- after "tank".

In the Claims

In Claim 17, line 33, replace "was" with --wash--.

In Claim 17, after line 37, insert

--1)      separating the d-Limonene from the aqueous wash water phase,--.

UNITED STATES PATENT AND TRADEMARK OFFICE
CERTIFICATE OF CORRECTION

PATENT NO. : 5,220,105
DATED : June 15, 1993
INVENTOR(S) : Kruger, Jr. et al.

It is certified that error appears in the above-identified patent and that said Letters Patent is hereby corrected as shown below:

<u>In the Claims (cont'd)</u>

In Claim 18, line 2, replace "J" with --j--.

In Claim 19, line 2, replace "J" with --j--.

Signed and Sealed this

Thirty-first Day of August, 1999

Attest:

Q. TODD DICKINSON

*Attesting Officer*    *Acting Commissioner of Patents and Trademarks*